United States Patent
Kiani

(10) Patent No.: US 12,251,545 B2
(45) Date of Patent: Mar. 18, 2025

(54) INJECTION ANALGESIA SYSTEM

(71) Applicant: Nessa Kiani, Laguna Niguel, CA (US)

(72) Inventor: Nessa Kiani, Laguna Niguel, CA (US)

( * ) Notice: Subject to any disclaimer, the term of this patent is extended or adjusted under 35 U.S.C. 154(b) by 149 days.

(21) Appl. No.: 17/653,352

(22) Filed: Mar. 3, 2022

(65) Prior Publication Data

US 2022/0296822 A1 Sep. 22, 2022

Related U.S. Application Data

(63) Continuation of application No. 16/228,048, filed on Dec. 20, 2018, now Pat. No. 11,298,468, which is a continuation of application No. 14/735,124, filed on Jun. 9, 2015, now Pat. No. 10,195,366.

(60) Provisional application No. 62/009,901, filed on Jun. 9, 2014.

(51) Int. Cl.
*A61M 5/42* (2006.01)

(52) U.S. Cl.
CPC ............ *A61M 5/422* (2013.01); *A61M 5/427* (2013.01)

(58) Field of Classification Search
CPC ........ A61M 5/427; A61M 5/422; A61M 5/42; A61M 25/0074; A61M 5/3287; A61M 2025/0057; A61M 5/425; A61M 1/08
See application file for complete search history.

(56) References Cited

U.S. PATENT DOCUMENTS

| | | | |
|---|---|---|---|
| 1,934,046 A | 11/1933 | Mario | |
| 4,943,284 A | 7/1990 | Erlich | |
| 10,195,366 B1 | 2/2019 | Kiani | |
| 11,298,468 B2 | 4/2022 | Kiani | |
| 2003/0078546 A1* | 4/2003 | Jensen | A61M 5/3202 604/232 |
| 2004/0147901 A1* | 7/2004 | Py | A61M 5/2033 604/176 |
| 2004/0199112 A1 | 10/2004 | Dalton | |
| 2007/0255234 A1* | 11/2007 | Haase | A61M 5/14276 604/288.01 |
| 2009/0234306 A1 | 9/2009 | Vitaris | |
| 2011/0166498 A1 | 7/2011 | Shantha | |

* cited by examiner

*Primary Examiner* — Scott J Medway
*Assistant Examiner* — Hamza A Darb
(74) *Attorney, Agent, or Firm* — Knobbe, Martens, Olson & Bear, LLP

(57) ABSTRACT

An injection analgesia system advantageously numbs a patient's skin around an injection site. An injection window guides a caregiver's injection placement to a relatively small area while allowing standard injection procedures to be followed, such as stretching the skin and puncturing the site with a jabbing motion. The injection analgesia system has a needle shield and an analgesia, which are layered together and applied to a skin surface. A needle shield window and a analgesia window align to form the injection window. Advantageously, the needle shield may fold and/or wrap around the injection needle for sharp object protection during and after needle disposal.

15 Claims, 6 Drawing Sheets

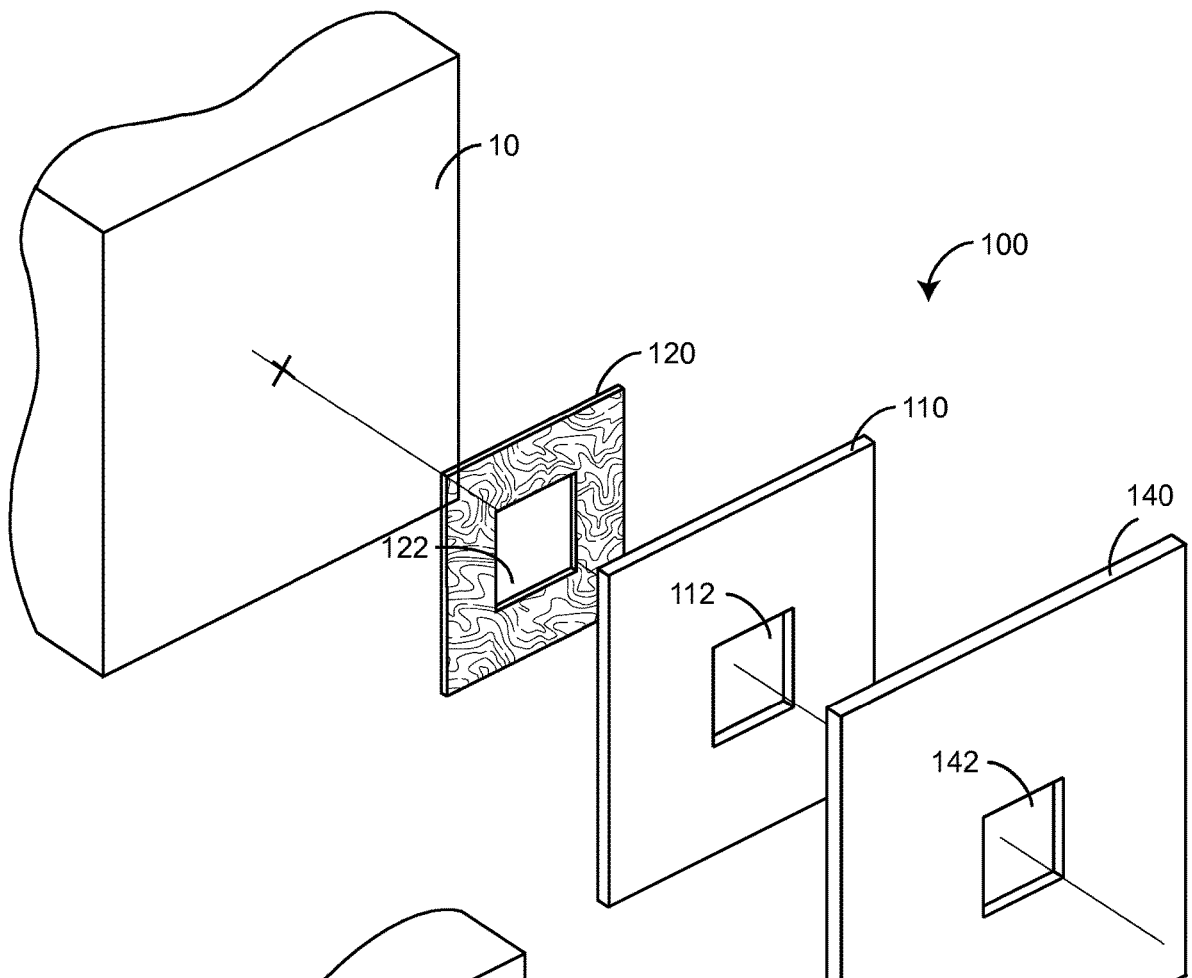
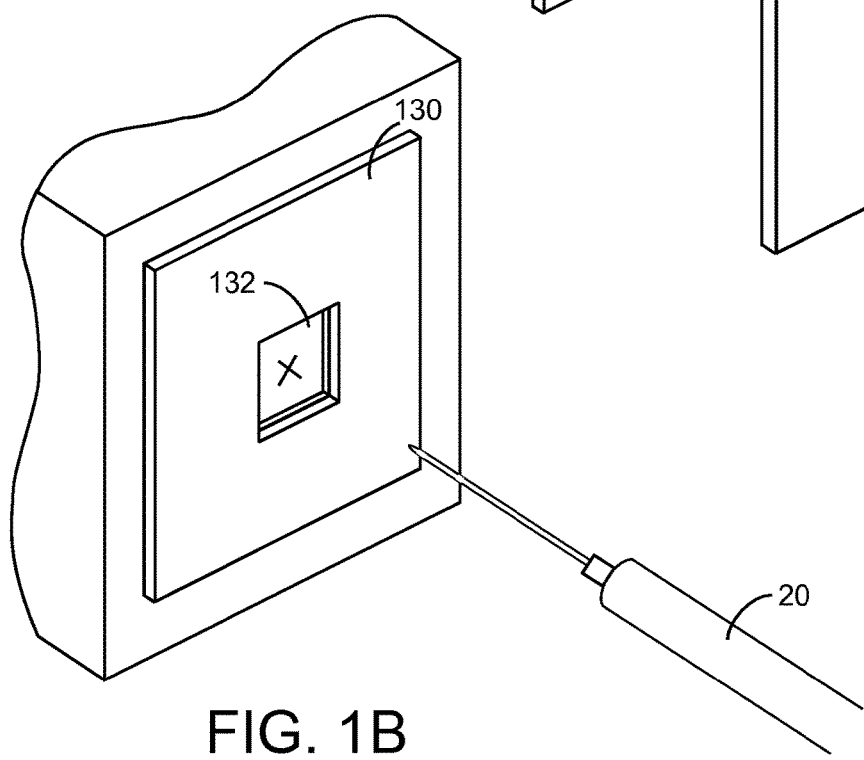
FIG. 1A
FIG. 1B

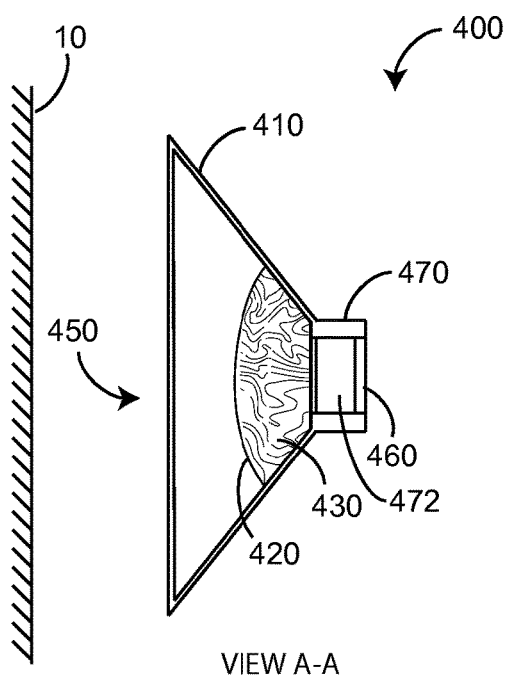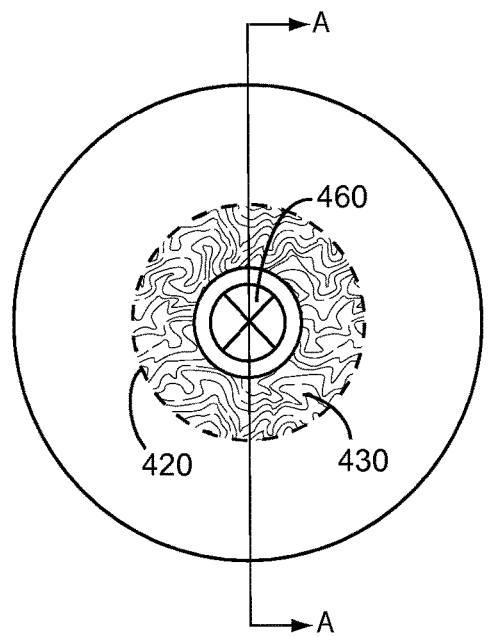
FIG. 4A  FIG. 4B
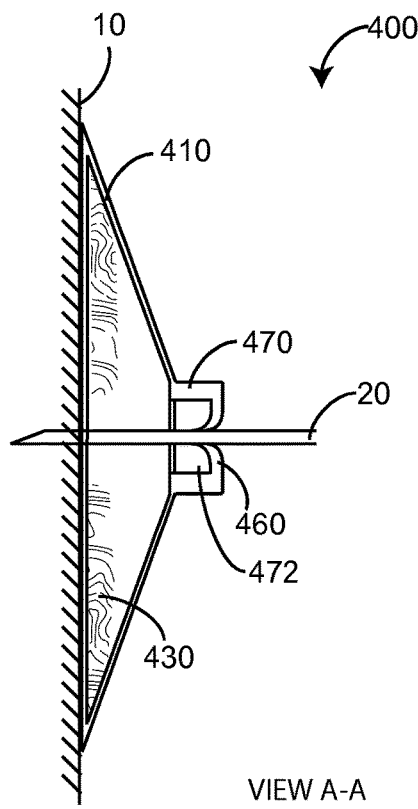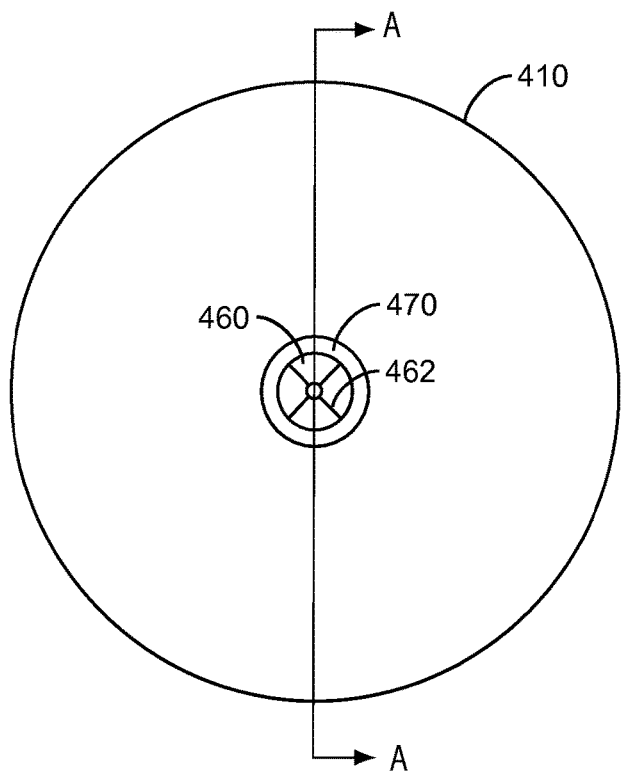
FIG. 4C  FIG. 4D

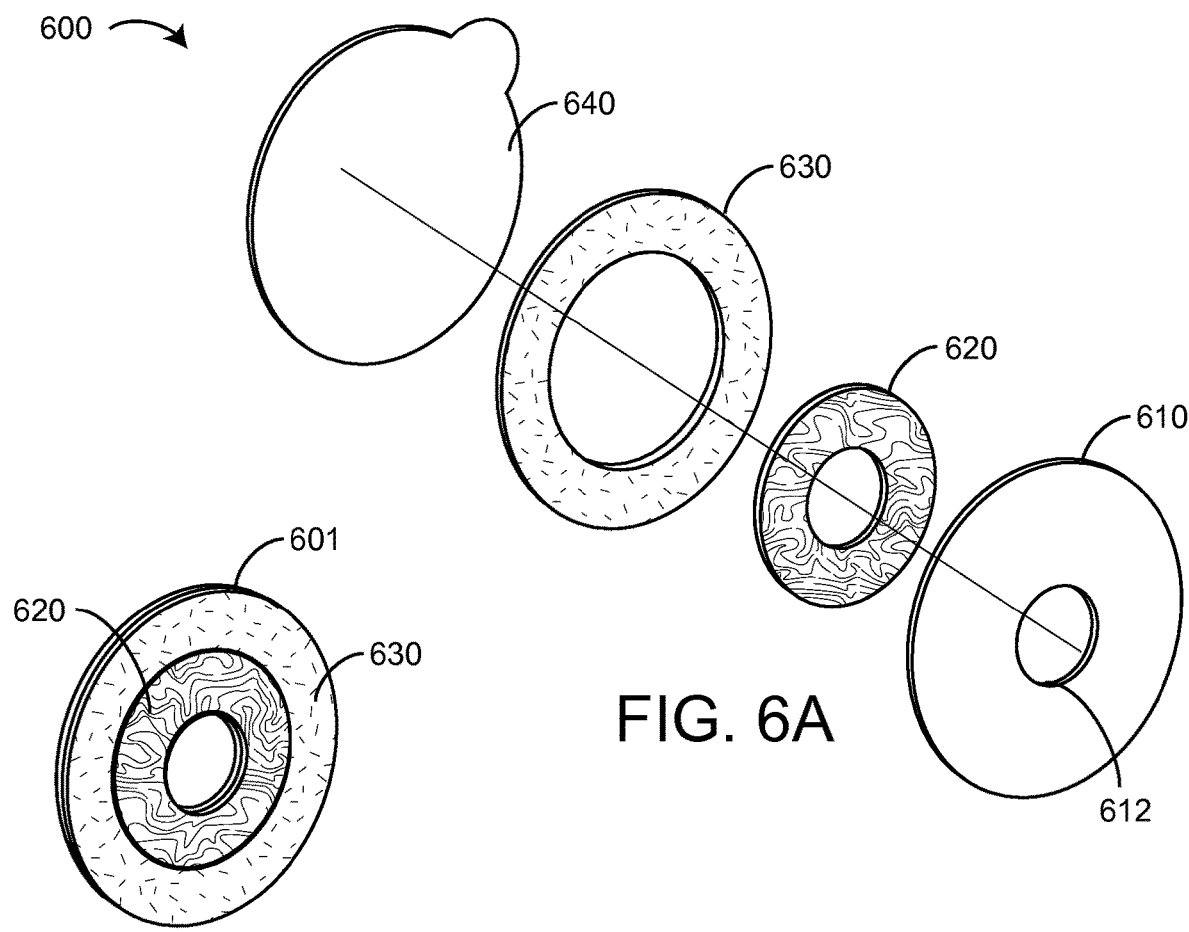
FIG. 6A
FIG. 6B
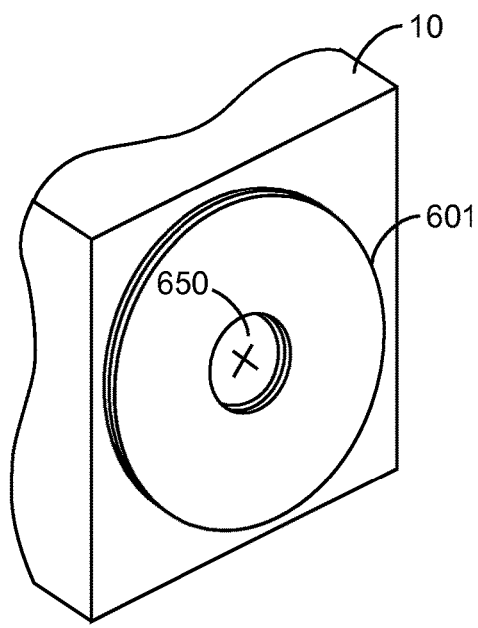
FIG. 6C

INJECTION ANALGESIA SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation of U.S. patent application Ser. No. 16/228,048, filed Dec. 20, 2018, entitled "INJECTION ANALGESIA SYSTEM", now U.S. Pat. No. 11,298,468, which is a continuation of U.S. patent application Ser. No. 14/735,124, filed Jun. 9, 2015, entitled "INJECTION ANALGESIA SYSTEM", now U.S. Pat. No. 10,195,366, which claims the benefit of priority to U.S. Provisional Patent Application No. 62/009,901, filed Jun. 9, 2014, entitled "INJECTION ANALGESIA SYSTEM".

SUMMARY OF THE INVENTION

One aspect of an injection analgesia system is to take pain away from flu shots and vaccines. A substantial portion of Americans are not vaccinated for prevalent and reoccurring communicable diseases, such as the flu. A major cause of this neglect is the pain associated with injection.

In an embodiment, an injection analgesia system has a flexible suction cup with an open front end and closed back end. A grip extends from the back end. A needle guide is disposed through the grip and into the suction cup. The needle guide is configured to guide an injection needle to an injection site. An analgesia is disposed within the suction cup. The analgesia is dispersed along a skin surface when the suction cup is attached to the skin surface, so as to reduce pain due to an injection.

In an embodiment, an injection analgesia system has a sealed adhesive patch with a needle shield layer defining a needle opening, an analgesia layer disposed proximate the opening, an adhesive layer disposed distal the opening and a removable backing disposed over the analgesia layer and adhesive layer. The backing is removed so as to unseal the adhesive layer and expose the analgesia layer to a skin surface.

In an embodiment, an injection analgesia system has a substrate with a first side and a second side. An opening is defined by the substrate. An analgesia is disposed on the second side proximate the opening, and an attachment mechanism is disposed proximate at least one of the substrate first side and the second side so as to secure the substrate second side to a skin surface and allow the analgesia to numb the skin surface proximate the opening. In various embodiments, the attachment mechanism is disposed proximate the second side. A second substrate is disposed proximate the first side and extends beyond the edges of the first substrate. An attachment mechanism is disposed proximate the outer edges of the second substrate so as to secure both the first substrate and the second substrate to the skin surface. The attachment mechanism may be disposed around the outer edges of the analgesia distal the opening. A backing layer is disposed over the analgesia and the adhesive distal the substrate. The backing layer protects the attachment mechanism from contamination and is removable prior to attachment of the substrate to the skin surface so as to expose the attachment mechanism and the analgesia to the skin surface. In various embodiments, the attachment mechanism is an adhesive or a suction cup.

In a further embodiment, an injection analgesia method provides a needle shield having a skin side and a needle side. An analgesia is disposed on a skin side. A needle guide is disposed on the needle side. The skin side is secure to an injection site so as to numb a person's skin prior to an injection. A needle is directed through the needle guide to the injection site. The securing mechanism may comprise compressing a suction cup to the injection site. In an embodiment, a needle path is disposed through a suction cup base and a breakable lid is disposed over the needle path so as to maintain a suction cup partial vacuum.

DESCRIPTION OF THE DRAWINGS

FIGS. 1A-B are exploded perspective and perspective views of a generalized injection analgesia system applied to a skin surface;

FIGS. 4A-D are un-mounted cross-sectional side and top views and mounted cross-sectional side and top views, respectively, of an analgesia capsule suction-cup embodiment of an injection analgesia system;

FIGS. 6A-C are front exploded perspective, back assembled perspective and mounted front perspective views, respectively, of an adhesive patch embodiment of an injection analgesia system.

DETAILED DESCRIPTION OF THE PREFERRED EMBODIMENT

Figure 2A:
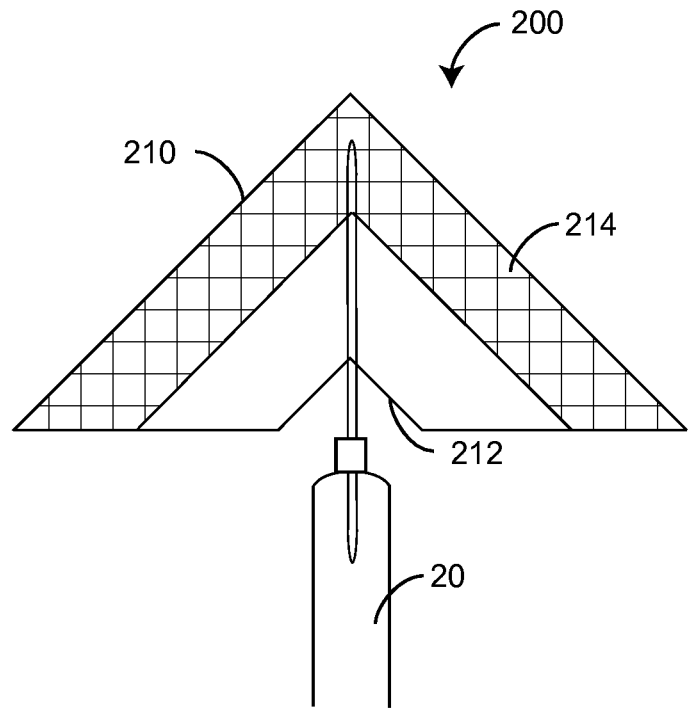
FIGS. 2A-B are folded and wrapped side-views, respectively, of an injection needle shield.

FIGS. 1A-B illustrate a generalized injection analgesia system 100 that advantageously numbs a patient's skin around an injection site. An injection window 132 advantageously guides a caregiver's injection placement to a relatively small area while allowing standard injection procedures to be followed, such as stretching the skin and puncturing the site with a jabbing motion. The injection analgesia system 100 has a needle shield 110 and an analgesia 120, which are layered together 130 and applied to a skin surface 10. A needle shield window 112 and a analgesia window 122 align to form the injection window 132. The needle shield 110 may be manufactured of various hygienic materials, such as medical-grade plastic, and a mild adhesive may be applied to the skin side of the shield 110 around the periphery of the analgesia 120 so as to removably adhere the shield 110 and analgesia 120 to the skin surface 10. Advantageously, the needle shield may fold and/or wrap around the injection needle for sharp object protection during and after needle disposal, as described with respect to FIGS. 2A-B, below.

As shown in FIGS. 1A-B, in an embodiment an attachment layer 140 having an attachment layer window 142 is disposed proximate needle shield 110 opposite the analgesia 120. The attachment layer 140 has adhesive disposed around the outer edges of the attachment layer 140, which extends beyond the edges of the needle shield 110. In this manner, the attachment layer 140 secures the needle shield 110 to the skin surface 10.

Figure 2B:
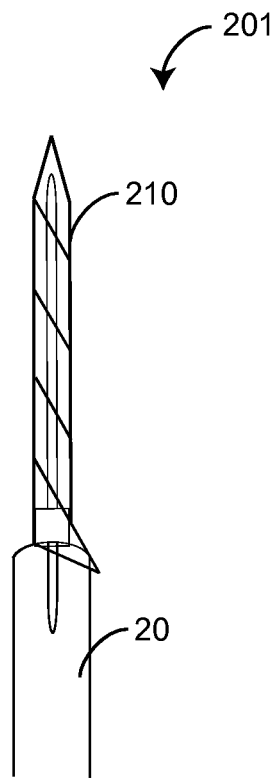

FIGS. 2A-B illustrate an injection needle shield 200 enclosing a used injection needle 20. FIGS. 2A-B are side-views of an injection analgesia system 200 after removal of a needle shield 210 from a skin surface and fully-enclosing the injection needle point by folding the needle shield 210 over the needle point (FIG. 2A) and, optionally, wrapping the shield 210 around the needle point (FIG. 2B). In an embodiment, the needle shield 200 has adhesive edges 214 allowing the folded shield 200 to adhere to itself so as to secure itself around the needle 20 as the needle extends through the shield window 212. In an embodiment, the needle shield 200 has interlocking extension disposed around the shield rim in lieu of or in addition to the adhesive 214, allowing portions of the needle shield to self-adhere and securely enclosing a substantial portion of the needle 20 and needle tip. In an embodiment, the needle shield 200 is in the form of a suction cup, such as described in detail with respect to FIGS. 3-5, below.

Figure 3A:
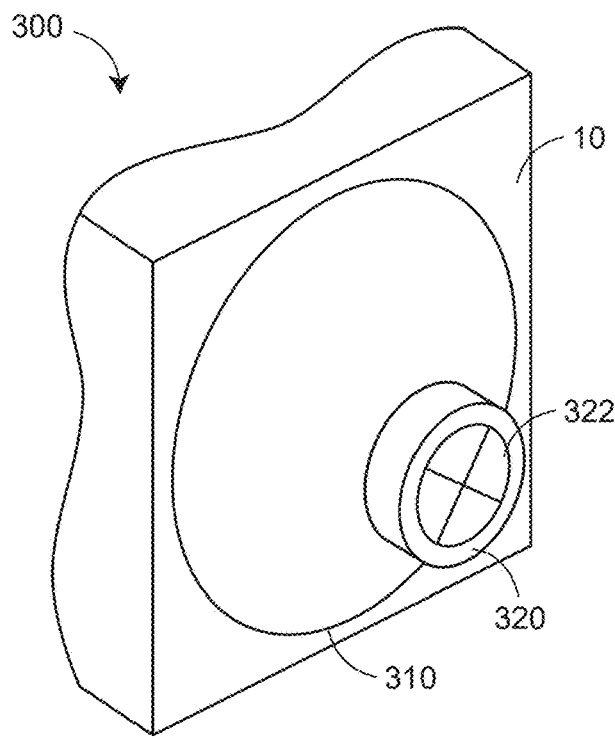
FIGS. 3A-B are mounted and injection perspective views, respectively, of a suction-cup embodiment of an injection analgesia system.
Figure 3B:
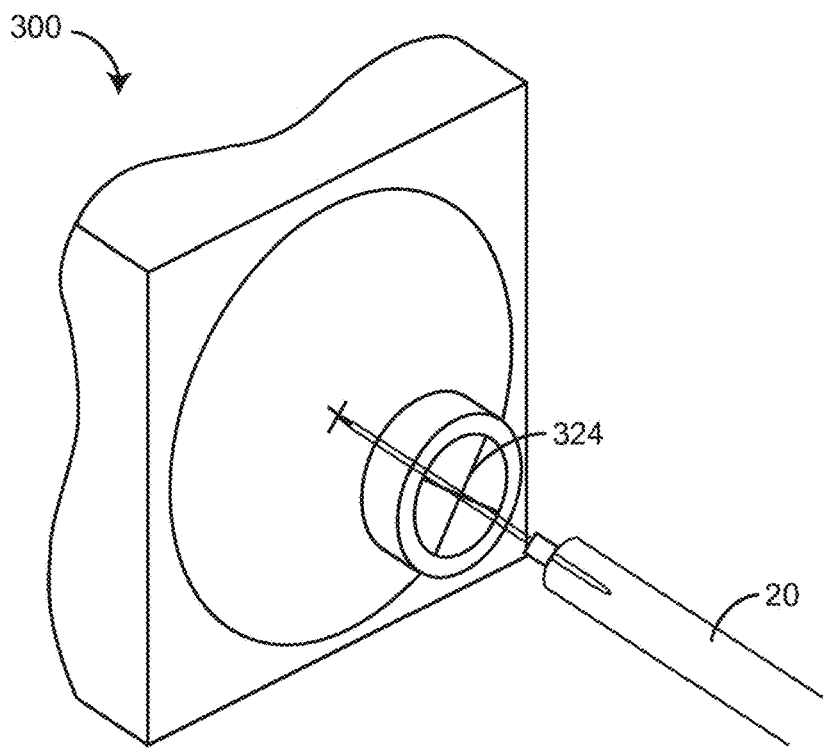

FIGS. 3A-B illustrate a suction-cup embodiment 300 of an injection analgesia system. The suction cup 300 has a flexible cup 310 and a rigid base 310 extending from the cup 310 center. The base 320 defines an opening 322 centrally disposed through the base 320 and extending into the cup 310. A scored lid 324 is disposed over the opening 322 so as maintain a partial vacuum when the suction cup 300 is pressed onto a skin surface 10. The scored lid 324 breaks when a needle 20 is jabbed, pressed or otherwise inserted into the opening 322 and into the skin so as to inject a serum or other medical fluid into a patient. Particular suction cup embodiments are described with respect to FIGS. 4-5, below.

FIGS. 4A-D illustrate an analgesia capsule suction-cup embodiment 400 of an injection analgesia system having a suction cup 410 needle shield. A capsule 420 is disposed within the suction cup 410 and an analgesia 430 is disposed within the capsule 420. As shown with respect to FIGS. 4A-B, the suction cup 410 has a generally conical shape with an open end 450 that tapers to a closed end 460. A generally cylindrical grip 470 is disposed on and extends from the closed end 460. A needle path 472 is centrally disposed through the cylindrical grip 470, and into the suction cup 410 proximate the analgesia capsule 430. As shown with respect to FIG. 4B, the closed end 460 is scored 462, holding a partial vacuum within the suction cup 410 until a needle pierces the closed end 460 during patient injection.

As shown with respect to FIGS. 4C-D, the suction cup 410 is applied to a skin surface 10 by grasping the grip 470 and pressing the suction cup 410 against the skin surface 10. In an embodiment, as the suction cup 410 expands against the skin surface 10, the capsule 420 bursts and the analgesia 430 is dispersed across the skin surface 10 and away from the cup 410 accordingly. After the analgesia has had time to take effect, the needle 20 is inserted through the scored lid 460 creating a needle opening 480. The needle 20 travels through the needle path 472 and into a patient's skin 10. In another embodiment, the capsule 420 is also disposed proximate the needle path 472 so that the needle 20 bursts the capsule 420 causing the analgesia 430 to disperse across the skin surface 10. In an embodiment, the needle path 172 serves as a guide to more accurately and steadily position the needle for injection.

Figure 5A:
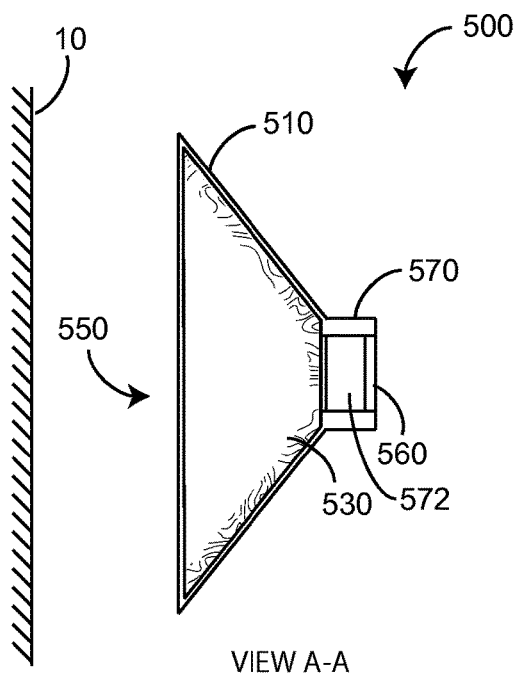
FIGS. 5A-D are un-mounted cross-sectional side and top views and mounted cross-sectional side and top views, respectively, of an analgesia film suction-cup embodiment of an injection analgesia system.
Figure 5B:
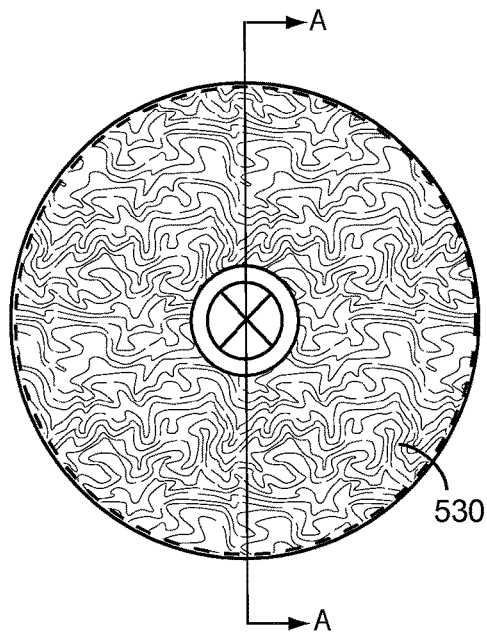
Figure 5C:
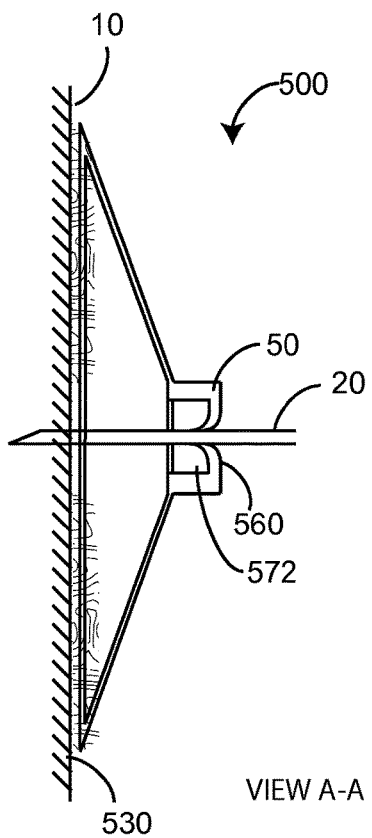
Figure 5D:
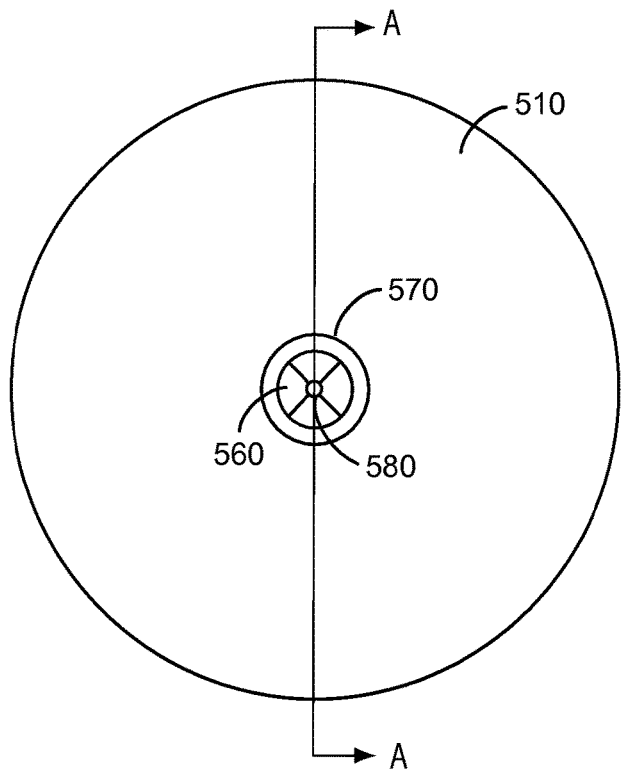

FIGS. 5A-D illustrate an analgesia film suction-cup embodiment 500 of an injection analgesia system. An analgesia 530 is pre-coated along the suction cup surface and contained by a tape or film (not shown) that removably adheres to the suction cup 510. The tape or film is removed prior to injection, and the analgesia is applied by over- extending the suction cup against the skin surface 10 and then releasing the suction cup to its normal applied position (FIG. 5C). After the analgesia 530 has had time to take effect, the needle 20 is inserted through the scored lid 560 creating a needle opening 580. The needle 20 travels through the needle path 572 and into a patient's skin 10.

FIGS. 6A-C illustrate an adhesive patch embodiment 600 of an injection analgesia system. As shown in FIG. 6A, an sealed adhesive patch 600 has an needle shield 610 defining a needle opening 612, an analgesia 620, an adhesive 630 and a removable backing 640. As shown in FIG. 6B, the backing 640 is removed so as to unseal an adhesive patch 601, exposing the analgesia 620 and adhesive 630 surfaces disposed on the needle shield 610. As shown in FIG. 6C, the exposed analgesia 620 and adhesive 630 surfaces of the adhesive patch 601 are pressed against a patient's skin 10 so as to adhere the adhesive patch 601 to the patient 10. After waiting a specified time period for the analgesia 620 to take affect, a painless injection is made through the patch window 650, the patch 601 removed and discarded.

An injection analgesia system has been disclosed in detail in connection with various embodiments. These embodiments are disclosed by way of examples only and are not to limit the scope of the claims that follow. One of ordinary skill in art will appreciate many variations and modifications.

What is claimed is:

1. A method of providing injection analgesia, the method comprising:
   providing a needle shield comprising a suction cup, the suction cup including a skin side and a needle side, the suction cup further including a skin contacting rim on a distal end of the suction cup;
   disposing an analgesia on the skin side of the suction cup;
   disposing a needle guide on the needle side, a distal end of the needle guide directly coupled to a proximal end of the suction cup, wherein the needle guide comprises a breakable scored lid on a proximal end of the needle guide opposite the distal end of the needle guide;
   securing the skin side of the suction cup to an injection site by securing the skin contacting rim of the suction cup onto a skin surface surrounding the injection site, an analgesic at the skin side configured to numb a person's skin enclosed within the skin contacting rim prior to an injection;
   creating a needle opening by directing a needle through the lid on the proximal end of the needle guide; and
   moving the needle toward the injection site.

2. The method according to claim 1 wherein securing the skin side of the suction cup to the injection site comprises compressing the suction cup to the injection site.

3. The method according to claim 2, wherein compressing the suction cup to the injection site comprises breaking a capsule at the skin side, the capsule containing the analgesia.

4. The method according to claim 1, wherein the suction cup is flexible such that compressing the suction cup to the injection site causes the suction cup to expand at the skin contacting rim.

5. The method according to claim 4, wherein the scored breakable lid and the expanded suction cup configured to maintain a partial pressure so as to secure the skin side of the suction cup to the injection site.

6. The method according to claim 1, wherein disposing the needle guide on the needle side comprises:
   forming a needle path through the needle guide; and
   disposing the lid over the needle path so as to maintain a suction cup partial vacuum.

7. The method according to claim 1, wherein directing the needle comprises breaking a capsule at the skin side, the capsule containing the analgesia.

8. The method according to claim 1, further comprising removing a backing layer disposed over a tape disposed on the skin side, the tape containing the analgesia.

9. A method of providing injection analgesia, the method comprising:
providing an injection analgesia system comprising a flexible suction cup, the flexible suction cup including a skin side and a needle side, the flexible suction cup further including a skin contacting rim on a distal end of the suction cup, the system further comprising a base, a distal end of the base coupled to a proximal end of the suction cup, a breakable scored lid located on a proximal end of the base opposite the distal end of the base;
disposing an analgesia on the skin side of the flexible suction cup;
securing the flexible suction cup by pressing the flexible suction cup against a skin surface of a patient and creating a partial pressure, the flexible suction cup being expanded upon being pressed against the skin surface, wherein the flexible suction cup being expanded and the breakable scored lid being located on the proximal end of the base are configured to maintain the partial pressure, and wherein the analgesia on the skin side is configured to numb the skin surface enclosed within the skin contacting rim; and
creating a needle opening by directing a needle through the breakable scored lid on the proximal end of the base; and
moving the needle toward the skin surface enclosed within the skin contacting rim.

10. The method according to claim 9, wherein the skin contacting rim of the flexible suction cup is disposed around outer edges of the analgesia that are distal to the breakable scored lid.

11. The method according to claim 9, wherein disposing the analgesia on the skin side of the flexible suction cup proximate the distal end comprises removably adhering an analgesia tape to the skin side of the flexible suction cup.

12. The method according to claim 11, further comprising removing a backing layer disposed over the analgesia tape prior to securing the flexible suction cup to the skin surface so as to expose the analgesia tape to the skin surface.

13. The method according to claim 9, wherein the analgesia is contained in an analgesia capsule.

14. The method according to claim 13, wherein the analgesia capsule is configured to break when pressing the flexible suction cup against the skin surface.

15. The method according to claim 13, wherein the analgesia capsule is configured to break when directing the needle to the skin surface enclosed within the skin contacting rim.

* * * * *